(12) United States Patent
Goto et al.

(10) Patent No.: US 6,197,290 B1
(45) Date of Patent: Mar. 6, 2001

(54) ANION EXCHANGE RESIN-CONTAINING TABLETS

(75) Inventors: Takeshi Goto; Tatsuya Meno, both of Ibaraki-ken (JP)

(73) Assignee: Hisamitsu Pharmaceutical Co., Inc., Sega-Ken (JP)

( * ) Notice: Subject to any disclaimer, the term of this patent is extended or adjusted under 35 U.S.C. 154(b) by 0 days.

(21) Appl. No.: 09/091,069

(22) PCT Filed: Oct. 15, 1997

(86) PCT No.: PCT/JP97/03720

§ 371 Date: Jan. 13, 1999

§ 102(e) Date: Jan. 13, 1999

(87) PCT Pub. No.: WO98/16237

PCT Pub. Date: Apr. 23, 1998

(30) Foreign Application Priority Data

Oct. 15, 1996 (JP) ..................................... 8-293328

(51) Int. Cl.⁷ .............................. A61K 9/36; A61K 47/32
(52) U.S. Cl. ............................................................ 424/78.1
(58) Field of Search ................................ 424/78.16, 78.1

(56) References Cited

U.S. PATENT DOCUMENTS

| 4,645,757 | 2/1987 | Hjerten et al. |
| 5,178,854 | 1/1993 | Asami et al. |

FOREIGN PATENT DOCUMENTS

| 2806707 | * 8/1978 | (DE) |
| 1-172324 | 7/1989 | (JP) |
| 2-286621 | 11/1990 | (JP) |
| 7-97330 | 4/1995 | (JP) |
| WO 97/04789 | 2/1997 | (WO) |

* cited by examiner

Primary Examiner—Peter F. Kulkosky
(74) Attorney, Agent, or Firm—David G. Conlin; Peter F. Corless; Edwards & Angell, LLP

(57) ABSTRACT

Disclosed are cholesterol-depressant, coated or non-coated tablets for oral administration, which comprise an anion exchange resin of formula (I):

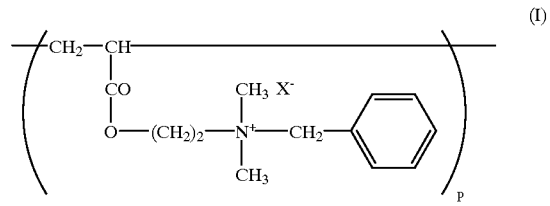

wherein X represents a physiologically-acceptable counter ion; and p represents an average degree of polymerization, and is larger than 10,000, silicon dioxide and crystalline cellulose, but not containing water. The non-coated tablets are preferably coated with cellulosic substances. The tablets are easy to take, as being not bitter. The dose of the tablets can be decreased, since the tablets can contain a large amount of the active ingredient. The mixture comprising the constituent components can be directly tabletted in the absence of water.

19 Claims, No Drawings

ANION EXCHANGE RESIN-CONTAINING TABLETS

TECHNICAL FIELD

The present invention relates to tablets and coated tablets which contain an anion exchange resin, especially a non-crosslinked anion exchange resin of a general formula (I) mentioned below, and which are useful as a cholesterol depressant. More precisely, it relates to those coated tablets with high stability, in which the content of the active ingredient is increased in order that they can be administered with ease and that the number of the tablets to be administered can be decreased.

In addition, the invention also relates to a method for producing the tablets and coated tablets.

BACKGROUND ART

Colestyramine of a crosslinked type, which is a conventional cholesterol depressant, is problematic in that its amount to be administered is large (8 to 16 g/day) and that it must be administered in the form of its suspension. Therefore, many studies have heretofore been made to produce tablets and coated tablets of anion exchange resins. For example, a method has been reported of coating tablets of a solid colestyramine resin having a water content of from 8 to 14% with a melt of polyethylene glycol and stearic acid in the presence of no solvent to give coated tablets, which do not swell in the mouth (see Japanese Patent Application Laid-Open No. 3-236326).

Regarding tablets of an imidazole-type anion exchange resin (see Japanese Patent Application Laid-Open No. 60-209523), known are a method of producing those tablets in the presence of a predetermined amount of water (see Japanese Patent Application Laid-open No. 2-286621); a method of producing coated tablets by coating those tablets as prepared in the presence of a predetermined amount of water, with hydroxypropyl cellulose or the like (see Japanese Patent Application No. 4-320155 (published before examination as Laid-Open No. 6-157325)); and a method of producing those tablets in the presence of a predetermined amount of water and silicon dioxide (see Japanese Patent Application Laid-Open No. 7-97330).

In addition, also known are methods of producing coated, anion exchange resin tablets with good moisture-resistant stability, which comprise tabletting an anion exchange resin in the presence of water to give non-coated tablets followed by coating them with a cellulosic substance or the like, and in which the hygroscopicity of the anion exchange resin in the non-coated tablets is lowered to thereby reduce the variation in the diameter of each non-coated tablet relative to the ambient humidity (see Japanese Patent Application Laid-Open Nos. 7-97330 and 6-157325). Those known methods are to coat the cores of non-coated tablets which contain a predetermined amount of water to thereby reduce the variation in the diameter in each non-coated tablet relative to the ambient humidity.

However, the conventional methods require the addition of a predetermined amount of water to the hygroscopic anion exchange resins being tabletted.

On the other hand, we, the present inventors have already reported that a non-crosslinked anion exchange resin of the formula (II):

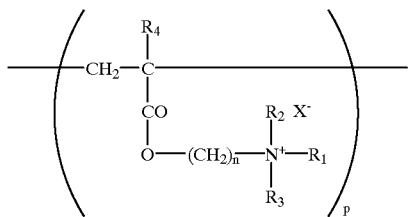

wherein $R_1$ represents an aralkyl group having from 7 to 10 carbon atoms, or an alkyl group having from 1 to 20 carbon atoms; $R_2$ and $R_3$ are the same or different and each independently represents a lower alkyl group having from 1 to 4 carbon atoms; $R_4$ represents a hydrogen atom or a lower alkyl group having from 1 to 4 carbon atoms; X represents a physiologically-acceptable counter ion; n represents an integer of from 1 to 3; and p represents an average degree of polymerization of from 10 to 10,000, is extremely useful as a cholesterol depressant (see WO93/13781). As being a non-crosslinked linear polymer, this anion exchange resin does not swell to increase its volume, unlike crosslinked polymers such as colestyramine, and therefore has no unfavorable side effects such as abdominal distention and constipation. In addition, the effective absorption of bile acid by the anion exchange resin per its unit weight is large. Accordingly, the anion exchange resin is very useful.

However, this resin is soluble in water and is highly bitter, and in addition, it is highly hygroscopic and deliquescent. Therefore, the novel, non-crosslinked cholesterol depressant comprising the compound of formula (II) is problematic in that, if tabletted in any of the conventional methods that require water in the mixing step, it is formed into tablets with poor strength and stability since its flowability and tablettability is very poor. Even if the cholesterol depressant comprising the compound of formula (II) is tabletted in the absence of water, the resulting tablets are still problematic in that they are very bitter because of the strong bitterness intrinsic to the compound of formula (II) itself. The dose of the compound of formula (II), though varying depending on the case to which it is administered, is relatively large or is generally from 0.1 to 9 g/day, preferably from 0.1 to 5 g/day. Tablets comprising the compound of formula (II) and containing a large amount of vehicles in order to reduce the bitterness of the compound are problematic in that the number of the tablets to be administered at a time shall be large.

In order to produce practical medicine products comprising the compound of formula (II) with such extremely high usefulness, it is desired to formulate the compound into highly-stable preparations without strong bitterness while adding thereto the smallest possible amount of vehicles as possible.

Having regard to the above problems, the present inventors already found that a mixture comprising the cholesterol depressant, non-crosslinked cation exchange resin of formula (II), along with at least silicon dioxide and crystalline cellulose could be formed into tablets in the absence of water on an industrial scale, that the cores of the thus-formed, non-coated tablets could be coated with a coating material comprising a cellulosic substance to give coated tablets, and that those coated tablets could overcome the problems in the art (see Japanese Patent Application No. 8-235718).

The non-crosslinked anion exchange resins of formula (II) have an average degree of polymerization of not larger than 10,000. As a result of additional studies, the inventors further found that non-crosslinked anion exchange resins of a general formula (I) mentioned below, having an average degree of polymerization of larger than 10,000, take excellent pharmaceutical effects as a cholesterol depressant.

The inventors still further found that the formulation of those resins of formula (I) involves the same problems as those in the formulation of the resins of formula (II) having an average degree of polymerization of from 10 to 10,000. In particular, the non-crosslinked anion exchange resins of formula (I) having an average degree of polymerization of larger than 10,000 are highly hygroscopic, therefore, the known tabletting methods requiring a predetermined amount of water were not directly applicable.

DISCLOSURE OF THE INVENTION

Having regard to the above-mentioned problems, the inventors have assiduously studied and, as a result, have found that a mixture comprising a non-crosslinked anion exchange resin of the following formula (I):

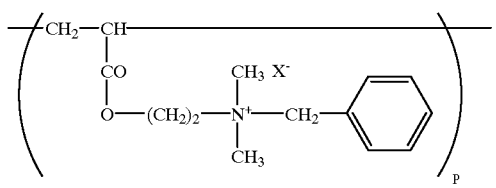

(I)

wherein X represents a physiologically-acceptable counter ion; and p represents an average degree of polymerization and is larger than 10,000,
and at least silicon dioxide and crystalline cellulose can be formed into tablets on an industrial scale, without adding water thereto, and that the cores of the non-coated tablets as obtained above can be coated with a coating agent comprising cellulose in order to coat the tablets, and also that those non-coated and coated tablets are free from the above-mentioned problems. In addition, the inventors have further found that, by that the non-coated tablets which are highly hygroscopic are coated with such a coating agent comprising cellulose, the coated tablets do not only control the bitter of the compound of formula (I) but also prevent hygroscopic of the non-coated tablets without adding water content. Therefore these tablets are stable in long-term storage.

The present invention provides anion exchange resin-containing tablets as formed by tabletting a mixture comprising the non-crosslinked anion exchange resin of formula (I) and at least silicon dioxide and crystalline cellulose but not containing water. The invention also provides a method for producing anion exchange resin-containing tablets, which comprises adding at least silicon dioxide and crystalline cellulose to the non-crosslinked anion exchange resin of formula (I) but not adding water thereto to give a mixture, followed by tabletting the mixture.

The invention further provides coated and non-crosslinked anion exchange resin containing tablets as produced by tabletting a mixture comprising the non-crosslinked anion exchange resin of formula (I) and at least silicon dioxide and crystalline cellulose but not containing water followed by coating the resulting non-coated tablets with a coating material comprising a cellulosic substance, and provides a method for producing such coated tablets.

The preparations of the invention are characterized in that they contain a minimized amount of vehicles, or that is, they contain a highest possible amount of the active ingredient.

The preparations of the invention can be produced in any continuous production lines on an industrial scale.

If the mixture to be tabletted into tablets according to the invention does not contain either one of silicon dioxide and crystalline cellulose, not only its tablettability is poor but also the fluctuation in the weight of the tablets formed is great, and in addition, the surfaces of the tablets formed are cracked and the edges thereof are chipped, resulting in that the yield of tablets with acceptable quality is greatly lowered (see Examples 4 and 5 in the present application).

BEST MODES OF CARRYING OUT THE INVENTION

The non-crosslinked anion exchange resin of formula (I) for use in the present invention is described in detail hereinunder.

The counter ion X in the non-crosslinked anion exchange resin of formula (I) for use in the invention is not specifically defined if it is a physiologically-acceptable counter ion. For this, however, preferred are halides, sulfates and phosphates; more preferred are halide ions such as chloride, bromide, fluoride and iodide ions.

The average degree of polymerization p of the non-crosslinked anion exchange resin of formula (I) for use in the invention is larger than 10,000, preferably from larger than 10,000 to 50,000, more preferably from larger than 10,000 to 30,000, even more preferably from larger than 10,000 to 15,000. More concretely, the average degree of polymerization p is preferably from 10,001 to 50,000, more preferably from 10,001 to 30,000, even more preferably from 10,001 to 15,000.

One preferred example of the non-crosslinked anion exchange resin of formula (I) for use in the invention is poly(acryloyloxyethyl-N,N-dimethyl-N-benzylammonium chloride) having an average degree of polymerization, p, of from 10,001 to 30,000, more preferably from 10,001 to 15,000.

In order to obtain an average degree of polimerization p, the ordinary ways may be performed, preferably the following way may be performed;

Firstly, a molecular weight was measured with GPC system apparatus (SHIMAZU SEISAKUSHO K.K.), RI (differential refractive index detection) as a detector and TOSOH G6000PWXL-G3000PWXL as a column, Column Temperature: 40° C.

Mobile Phase: 50 mM-NaCl solution

Flow Rate: 1 mL/min.

and then the measured molecular weight was divided by a basic structure unit (a molecular weight of monomer).

The non-crosslinked anion exchange resin of formula (I) for use in the invention can be produced in any ordinary method in which the corresponding monomers are prepared and then polymerized in an ordinary manner. More concretely, quaternary ammonium salts of the corresponding monomers are prepared and are polymerized to a sufficient degree in the presence of a polymerization initiator such as a radical polymerization initiator. If the polymerization is effected under a mild condition, the resulting polymer may have a small average degree of polymerization, p. Therefore, it is desired to effect the polymerization to a sufficient degree.

Now, the preparations of the invention are described hereinunder.

The amount of the compound of formula (I) to be in the non-coated tablets of the invention may be from 50 to 95% by weight, preferably from 70 to 90% by weight, more preferably from 75 to 90% by weight, relative to the total weight of each non-coated tablet.

Silicon dioxide and crystalline cellulose to be used in the invention are not specifically defined, provided that their oral administration is admitted. From the commercial viewpoint, however, preferred are those which have heretofore been used in conventional oral medicines.

Silicon dioxide is to well fluidize the mixture to be tabletted. For example, employable is colloidal silicon dioxide hydrate (e.g., white carbon), silicon dioxide (e.g., silica gel, silicic anhydride) and so on. Preferred is anhydrous, fine particulate silicon dioxide or light silicic anhydride. Silicon dioxide for use in the invention has an apparent specific gravity of from 20 g/liter to 70 g/liter, preferably from 20 g/liter to 50 g/liter. Preferred is light silicic anhydride having a small apparent specific gravity. The amount of silicon dioxide to be added may be from 0.01 to 5% by weight, preferably from 0.1 to 3% by weight, more preferably from 0.1 to 1% by weight, relative to the total weight of each non-coated tablet.

Crystalline cellulose is preferably microcrystalline cellulose, and may have a mean grain size of from 5 to 50 microns, preferably from 10 to 50 microns, more preferably from 10 to 30 microns. Its amount to be added may be from 0.1 to 30% by weight, preferably from 1 to 30% by weight, more preferably from 10 to 30% by weight, relative to the total weight of each non-coated tablet.

Regarding silicon dioxide, especially light silicic anhydride added to the mixture to be tabletted in the invention, the increase in its amount and the decrease in its apparent specific gravity (bulk density) results in the increase in the fluidity of the powdery mixture, while often worsening the tablettability (into compact tablets) of the mixture. Therefore, if silicon dioxide is added to the mixture in an amount of 5 parts or more, relative to the compound of formula (I), the tablettability of the mixture is poor thereby resulting in that the tablets formed are much cracked.

On the other hand, regarding crystalline cellulose added to the mixture to be tabletted in the invention, the increase in its amount and the decrease in its mean grain size results in the increase in the tablettability (into compact tablets) of the powdery mixture, while often lowering the fluidity of the mixture. In particular, if crystalline cellulose is added to the mixture in an amount of larger than 30 parts relative to the compound of formula (I), the weight of the tablets formed greatly fluctuates. Since there is no significant reason for adding crystalline cellulose to the mixture in such an amount of larger than 30 parts, it is desirable to add any inexpensive vehicle such as lactose to the mixture if the addition of a large amount of vehicles is needed.

Discussing it in more detail, the invention provides anion exchange resin-containing tablets as formed by tabletting a mixture comprising the non-crosslinked anion exchange resin of formula (I), and containing at least light silicic anhydride having a small apparent specific gravity of from 20 g/liter to 70 g/liter, preferably from 20 g/liter to 50 g/liter, and crystalline cellulose having a mean grain size of from 10 microns to 50 microns, preferably from 10 microns to 30 microns, but not containing water, and provides a method for producing the tablets.

Also in more detail, the invention provides anion exchange resin-containing tablets as formed by tabletting a mixture comprising the non-crosslinked anion exchange resin of formula (I), and containing at least silicon dioxide having a small apparent specific gravity of from 20 g/liter to 50 g/liter, preferably from 20 g/liter to 40 g/liter, and crystalline cellulose having a mean grain size of from 10 microns to 50 microns, preferably from 10 microns to 30 microns, but not containing water, in which the anion exchange resin is from 50 to 95% by weight, preferably from 70 to 90% by weight, more preferably from 75 to 90% by weight, relative to the total weight of each tablet, and provides a method for producing the tablets.

The invention further provides coated, non-crosslinked anion exchange resin-containing tablets as produced by coating the non-coated tablets with a coating material comprising a cellulosic substance, and provides a method for producing the coated tablets.

The non-coated tablets of the invention, which may be the cores of the coated tablets, may contain, in addition to the above-mentioned silicon dioxide and crystalline cellulose, any other conventional additives that are generally employable in forming tablets, within the range not interfering with the object of the invention. For example, the tablets of the invention may optionally contain any of vehicles, for example, bioses and monoses such as lactose, sucrose, glucose, mannitol and sorbitol, and starches such as potato starch, wheat starch, corn starch and rice starch; lubricants, for example, inorganic substances such as calcium phosphate and calcium sulfate, higher fatty acids and their metal salts (e.g., stearic acid, magnesium stearate), higher alcohols, talc, and synthetic aluminium silicate; disintegrators such as starches, sodium or potassium salt of carboxymethyl cellulose, methyl cellulose, carboxymethyl starch and sodium alginate; and binders such as starches, sucrose, gelatin, arabic gum, methyl cellulose, sodium carboxymethyl cellulose, polyvinyl pyrrolidone and polymethyl pyrrolidone.

The non-coated tablets of the invention, which may be the cores of the coated tablets, can be produced by mixing the constituent components and tabletting the resulting mixture. The order of adding the components to give the mixture is not specifically defined. Preferably, however, crystalline cellulose and silicon dioxide are first mixed, and then the compound of formula (I) is added thereto preferably gradually, and mixed together. Then, the optional components may be added to and mixed with the resulting mixture.

The tabletting pressure is not specifically defined, but is preferably not larger than 2 tons.

The cellulosic substance to be in the coating material which is used in coating the non-coated tablets in the invention is not specifically defined, provided that it is a pH-independent and water-soluble one. Concretely, for example, employable are hydroxypropyl cellulose, hydroxypropylmethyl cellulose, and methyl cellulose. Preferred is hydroxypropylmethyl cellulose.

Those cellulosic substances may be used singly, but if desired, may be used along with a small amount of wax, titanium oxide, talc, hydroxypropyl cellulose with a low degree of substitution, polyethylene glycol, triethyl citrate or the like. In view of the strength of the coated film and of the economical aspect, polyethylene glycol (Macrogol) is preferably added to the coating material.

Regarding the concentration of the cellulosic substance in the coating liquid, if it is too high, the amount of the cellulosic substance to be in the coated film is too much. Therefore, too high concentration of the cellulosic substance in the coating liquid is unfavorable. Preferably, the concentration of the cellulosic substance is smaller than 20% by weight, more preferably from 6 to 15% by weight or so. Where polyethylene glycol (Macrogol) is added to the coating liquid, its concentration is preferably from 1 to 50% by weight or so, more preferably from 5 to 40% by weight or so, relative to the cellulosic substance.

Acid-soluble, film-forming substances are also employable for coating the non-coated tablets. For example, employable are coating materials capable of dissolving in gastric acids, such as diethylamino methacrylate, polyvinyl acetal diethylaminoacetate (AEA), dimethylaminoethyl methacrylate-methyl methacrylate copolymer (be on the market as EUDRAGIT (methyl methacrylate-butyl methacrylate-dimethylaminoethyl methacrylate copolymer)), cellulose acetate N,N-di-n-butylhydroxypropyl ether (CABP), etc.

The coating method is not specifically defined, but preferred is spray-coating.

The amount of the coating material to be applied to the non-coated tablets is preferably such that the coated film may be from 1 to 10% by weight relative to each non-coated tablet (core). To mask the bitterness of the non-coated tablets, the tablets may be coated with the coated film of 1% by weight or more. However, even if the tablets are coated with the film of larger than 10% by weight, such produces no more advantages. Most preferably, the coated film is about 3% by weight. Prior to coating them, it is preferable to measure the water content of the non-coated tablets (cores), and the coating is continued until the increase in the water content of the coated tablets is no more recognized.

EXAMPLES

Now, the invention is described in more detail hereinunder with reference to the following Examples. However, it is obvious that the invention is not restricted by those Examples but may encompass any other changes and modifications without overstepping its scope and spirit.

Example 1

(1) Mixing Step:

To mix the constituent components, used was the following mixing device.

Mixing Device: V-type mixer, FMV100 (POWREX)

(1-1) Mixing Method:

As in the mixture formulation mentioned below, 1000 g of crystalline cellulose and 50 g of light silicic anhydride were weighed, put into the mixer, and mixed therein for 5 minutes.

The total amount of poly(acryloyloxyethyl-N,N-dimethyl-N-benzylammonium chloride) (of formula (I) where X is chloride ion—hereinafter referred to as "compound 1") having an average degree of polymerization of 12,000 was divided into four portions, which were separately added to the mixture one after another at intervals of 5 minutes, with still mixing it.

Next, 50 g of magnesium stearate was weighed, added to the mixture and further mixed for 1 minute.

(1-2) Mixture Formulation (10 kg):

| | |
|---|---|
| Compound 1 | 8900 g |
| Crystalline Cellulose | 1000 g |
| (be on the market as Avicel PH-F20 (average grain size: 17 microns)) | |
| Magnesium Stearate | 50 g |
| Light Silicic Acid | 50 g |
| (apparent specific gravity (bulk density): 30 g/liter) | |

(2) Tabletting Step:

To form the mixture into tablets, used was the following tabletting device:

Tabletting Device: Rotary tabletting machine, HT-AP15SS (Hata Ironworks Co.)

(2-1) Tabletting Condition

| | |
|---|---|
| Number of revolution: | 35 rpm |
| Thickness of tablet: | 5 mm |
| Hardness of tablet: | 7 or more |
| Vertical pressure for tabletting: | 2 tons or less |
| Feeding system: | forced feeder used |

(3) Coating Step:

To coat the non-coated tablets, used was the following coating device:

Coating Device: Dria Coater 650 (POWREX)

(3-1) Coating Method:

7 kg of the non-coated tablets produced in the previous step (2) were put into a coating pan, in which the temperature of the vapor to be absorbed by the tablets was kept at 80° C. without revolving the pan (number of revolution: 0 rpm) until the temperature of the vapor as discharged from the pan became constant. In this stage, the temperature of the discharged vapor was confirmed to be 50° C. or higher. 20 tablets were sampled out of the pan and weighed. Then, they were ground, and their water content was measured. After this, a coating liquid having the composition mentioned below was sprayed over the tablets in the pan at a spraying rate of 12 g/min, while the pan was revolved at 7 rpm. After 30 minutes, the number of revolution of the pan was changed to 15 rpm, and the spraying was further continued at a spraying rate of about 18 g/min. At regular intervals during the spraying, 20 tablets were sampled out, and their weight and water content were measured. When no increase in the water content of the sampled, coated tablets was recognized and when the weight of the coated tablets became 103% of the non-coated tablets, the spraying was stopped. Then, the pan was still revolved at 5 rpm for about 60 minutes to dry the coated tablets.

(3-2) Coating Liquid Formulation:

| | |
|---|---|
| Hydroxypropylmethyl Cellulose 2910 | 400 g |
| Macrogol 6000 | 120 g |
| Ion-exchanged Water | 4600 g |

Example 2

(1) Mixing Step:

To mix the constituent components, used was the following mixing device.

Mixing Device: V-type mixer, FMV100 (POWREX)

(1-1) Mixing Method:

As in the mixture formulation mentioned below, 2000 g of crystalline cellulose and 50 g of light silicic anhydride were weighed, put into the mixer, and mixed therein for 5 minutes.

The total amount of compound 1 was divided into four portions, which were separately added to the mixture one after another at intervals of 5 minutes, with still mixing it.

Next, 50 g of magnesium stearate was weighed, added to the mixture and further mixed for 1 minute.

(1-2) Mixture Formulation (10 kg)

| | |
|---|---|
| Compound 1 | 7900 g |
| Crystalline Cellulose | 1000 g |
| (be on the market as Avicel PH-310 (average grain | |

-continued

| | |
|---|---|
| size: 40 microns)) | |
| Magnesium Stearate | 50 g |
| Light Silicic Acid | 50 g |
| (apparent specific gravity (bulk density): 50 g/liter) | |

(2) Tabletting Step, Coating Step:

In the same manner as in Example 1, the mixture was tabletted and coated.

Example 3

(1) Mixing Step:

To mix the constituent components, used was the following mixing device.

Mixing Device: V-type mixer, FMV100 (POWREX)

(1-1) Mixing Method:

As in the mixture formulation mentioned below, 1000 g of crystalline cellulose, 550 g of lactose and 50 g of light silicic anhydride were weighed, put into the mixer, and mixed therein for 5 minutes.

The total amount of compound 1 was divided into four portions, which were separately added to the mixture one after another at intervals of 5 minutes, with still mixing it.

Next, 50 g of magnesium stearate was weighed, added to the mixture and further mixed for 1 minute.

(1-2) Mixture Formulation (10 kg):

| | |
|---|---|
| Compound 1 | 8350 g |
| Crystalline Cellulose | 1000 g |
| (be on the market as Avicel PH-F20 (average grain size: 17 microns)) | |
| Lactose | 550 g |
| Magnesium Stearate | 50 g |
| Light Silicic Acid | 50 g |
| (apparent specific gravity (bulk density): 50 g/liter) | |

(2) Tabletting Step, Coating Step:

In the same manner as in Example 1, the mixture was tabletted and coated.

Example 4

(1) Mixing Step, Tabletting Step:

In the same manner as in Example 1, the constituent components were mixed and tabletted.

(2) Coating Step:

(2-1) Coating Method:

In the same manner as in Example 1, the non-coated tablets were coated with the coating liquid mentioned below, and then dried. Next, 5 g of carnauba wax was added to the coating pan still containing the dried, coated tablets therein, and the pan was further revolved at 5 rpm for 5 minutes.

(2-2) Coating Liquid Formulation:

| | |
|---|---|
| Hydroxypropylmethyl Cellulose 2910 | 400 g |
| Macrogol 6000 | 120 g |
| Titanium Oxide | 28 g |
| Ion-exchanged Water | 4000 g |

(2-3) Lubricant:

| | |
|---|---|
| Powdery Carnauba Wax | 5 g |

Example 5

Non-coated tablets were produced in the same manner as in Example 1-(1) and (2), except that poly(acryloyloxyethyl-N,N-dimethyl-N-benzylammonium chloride (of formula (I) where X is chloride ion)) having an average degree of polymerization of 13,000 was used. Next, these were coated in the same manner as in Example 1-(3) to obtain coated tablets.

Example 6

Non-coated tablets were produced in the same manner as in Example 1-(1) and (2), except that poly(acryloyloxyethyl-N,N-dimethyl-N-benzylammonium chloride (of formula (I) where X is chloride ion)) having an average degree of polymerization of 15,000 was used. Next, these were coated in the same manner as in Example 1-(3) to obtain coated tablets.

Comparative Example 1

(1) Mixing Step:

To mix the constituent components, used was the following mixing device.

Mixing Device: V-type mixer, FMV100 (POWREX)

(1-1) Mixing Method:

As in the mixture formulation mentioned below, 1000 g of crystalline cellulose and 50 g of light silicic anhydride were weighed, put into the mixer, and mixed therein for 5 minutes.

The total amount of compound 1 was divided into four portions, which were separately added to the mixture one after another at intervals of 5 minutes, with still mixing it.

Next, 50 g of magnesium stearate was weighed, added to the mixture and further mixed for 1 minute.

Since it was difficult to mix compound 1 and water, 890 g of water sprayed over the system being mixed.

(1-2) Mixture Formulation (10 kg):

| | |
|---|---|
| Compound 1 | 8010 g |
| Water | 890 g |
| Crystalline Cellulose | 1000 g |
| (be on the market as Avicel PH-F20 (average grain size: 17 microns)) | |
| Magnesium Stearate | 50 g |
| Light Silicic Acid | 50 g |
| (apparent specific gravity (bulk density): 30 g/liter) | |

Comparative Example 2

(1) Mixing Step:

To mix the constituent components, used was the following mixing device.

Mixing Device: V-type mixer, FMV100 (POWREX)

(1-1) Mixing Method:

As in the mixture formulation mentioned below, 1000 g of crystalline cellulose and 50 g of light silicic anhydride were weighed, put into the mixer, and mixed therein for 5 minutes.

The total amount of compound 1 was divided into four portions, which were separately added to the mixture one after another at intervals of 5 minutes, with still mixing it.

Next, 50 g of magnesium stearate was weighed, added to the mixture and further mixed for 1 minute.

(1-2) Mixture Formulation (10 kg):

| | |
|---|---|
| Compound 1 | 8900 g |
| Crystalline Cellulose | 1000 g |
| (be on the market as Avicel PH-301 (average grain size: 40 microns)) | |
| Magnesium Stearate | 50 g |
| Light Silicic Acid | 50 g |
| (apparent specific gravity (bulk density): 30 g/liter) | |

(2) Tabletting Step, Coating Step:

In the same manner as in Example 1, the mixture was tabletted and coated.

Comparative Example 3

(1) Mixing Step:

To mix the constituent components, used was the following mixing device.

Mixing Device: V-type mixer, FMV100 (POWREX)

(1-1) Mixing Method:

As in the mixture formulation mentioned below, 1000 g of crystalline cellulose and 50 g of light silicic anhydride were weighed, put into the mixer, and mixed therein for 5 minutes.

The total amount of compound 1 was divided into four portions, which were separately added to the mixture one after another at intervals of 5 minutes, with still mixing it.

Next, 50 g of magnesium stearate was weighed, added to the mixture and further mixed for 1 minute.

(1-2) Mixture Formulation (10 kg):

| | |
|---|---|
| Compound 1 | 8900 g |
| Crystalline Cellulose | 1000 g |
| (be on the market as Avicel PH-302 (average grain size: 120 microns)) | |
| Magnesium Stearate | 50 g |
| Light Silicic Acid | 50 g |
| (apparent specific gravity (bulk density): 30 g/liter) | |

(2) Tabletting Step, Coating Step:

In the same manner as in Example 1, the mixture was tabletted and coated.

Comparative Example 4

(1) Mixing Step:

To mix the constituent components, used was the following mixing device.

Mixing Device: V-type mixer, FMV100 (POWREX)

(1-1) Mixing Method:

As in the mixture formulation mentioned below, 50 g of light silicic anhydride was weighed and put into the mixer.

The total amount of compound 1 was divided into four portions, which were separately added to the anhydride one after another at intervals of 5 minutes, with mixing it.

Next, 50 g of magnesium stearate was weighed, added to the mixture and further mixed for 1 minute.

(1-2) Mixture Formulation (10 kg):

| | |
|---|---|
| Compound 1 | 9900 g |
| Magnesium Stearate | 50 g |
| Light Silicic Acid | 50 g |
| (apparent specific gravity (bulk density): 30 g/liter) | |

(2) Tabletting Step, Coating Step:

In the same manner as in Example 1, the mixture was tabletted and coated.

Comparative Example 5

(1) Mixing Step:

To mix the constituent components, used was the following mixing device.

Mixing Device: V-type mixer, FMV100 (POWREX)

(1-1) Mixing Method:

As in the mixture formulation mentioned below, 1000 g of crystalline cellulose was weighed and put into the mixer.

The total amount of compound 1 was divided into four portions, which were separately added to the crystalline cellulose one after another at intervals of 5 minutes, with mixing it.

Next, 50 g of magnesium stearate was weighed, added to the mixture and further mixed for 1 minute.

(1-2) Mixture Formulation (10 kg):

| | |
|---|---|
| Compound 1 | 8950 g |
| Crystalline Cellulose | 1000 g |
| (trade name: Avicel PH-F20 (average grain size: 17 microns)) | |
| Magnesium Stearate | 50 g |

(2) Tabletting Step, Coating Step:

In the same manner as in Example 1, the mixture was tabletted and coated.

Comparative Example 6

(1) Mixing Step:

To mix the constituent components, used was the following mixing device.

Mixing Device: V-type mixer, FMV100 (POWREX)

(1-1) Mixing Method:

As in the mixture formulation mentioned below, 9950 g of compound 1 and 50 g of magnesium stearate were weighed, put into the mixer, and mixed therein for 1 minute.

(1-2) Mixture Formulation (10 kg):

| | |
|---|---|
| Compound 1 | 9950 g |
| Magnesium Stearate | 50 g |

(2) Tabletting Step, Coating Step:

In the same manner as in Example 1, the mixture was tabletted and coated.

Comparative Example 7

Non-coated tablets were produced in the same manner as in Example 1, but these were not coated herein.

Test Example 1

The samples prepared above were tested for their powder flowability and compressibility (tablettability). As in Table 1, the fluctuation in the weight of non-coated tablets indicates the powder flowability, and the frequency of chipping and cracking of coated tablets, for which the non-coated tablets were produced by compressing the powdery mixture at a pressure of 2 tons or lower, indicates the compressibility. Since the non-coated tablets were highly hygroscopic, their weight increased in the abrasion test. The outward appearance of the tested tablets indicates their compressibility.

The test data are shown in Table 1.

TABLE 1

| | Fluctuation in Weight of Non-coated Tablets | Chipping, Cracking | Tablettability |
|---|---|---|---|
| Example 1 | small | no | A |
| Example 2 | small | no | A |
| Example 3 | small | no | A |
| Comparative Example 1 | untablettable | — | — |
| Comparative Example 2 | small | surface cracked | C |
| Comparative Example 3 | small | surface cracked, edges chipped | C |
| Comparative Example 4 | small | surface cracked, edges chipped | C |
| Comparative Example 5 | medium | no | B |
| Comparative Example 6 | great | surface cracked, edges chipped | D |

In Comparative Example 1 in which the components were mixed along with water, the components could not be well mixed because of their deliquescence and cobwebbing, and could not be tabletted.

In all Examples and Comparative Examples in which the components were mixed in the absence of water, it was possible to tablet the mixtures and coat the non-coated tablets. However, only samples in Example 1, Example 2 and Example 3 involved no problem with respect to their powder flowability and compressibility.

In Comparative Example 4, crystalline cellulose was not used; in Comparative Example 5, light silicic anhydride was not used; and in Comparative Example 6, both the two were not used. In the absence of crystalline cellulose, the tablettability (compressibility) of the mixture is extremely poor, and the surface of the coated tablets was cracked. In the absence of light silicic anhydride, the powder flowability of the mixture was poor, and the fluctuation in the weight of the tablets increased. In the absence of the two, crystalline cellulose and light silicic anhydride, the fluctuation in the weight of the tablets greatly increased, and the tablets were cracked and chipped, or that is, the tablettability of the mixture was poor.

In Comparative Example 2, crystalline cellulose having a mean grain size of 40 microns was used; and in Comparative Example 3, crystalline cellulose having a mean grain size of 120 microns was used. In those two, used was light silicic anhydride having an apparent specific gravity (bulk density) of 30 g/liter. Even though crystalline cellulose having a large mean grain size was used, the mixture could be tabletted if light silicic anhydride having a small apparent specific gravity (bulk density) was added thereto (see Example 2). However, as in those Comparative Examples, if light silicic anhydride having a large apparent specific gravity (bulk density) was added to the mixture, it is known that the tablets were cracked or chipped and the tablettability of the mixture was poor.

As in Example 1 in which were used light silicic anhydride having a small apparent specific gravity (bulk density) and crystalline cellulose having a small mean grain size, the tablets formed had a high chemical (active ingredient) content. Thus, the tablets of the invention are advantageous in that the dose of the tablets can be decreased. In addition, the mixture formulation for the tablets of the invention can be stably tabletted in continuous production plants directly after the step of mixing it, without requiring any additional step of granulating it.

Test Example 2

The tablets of the invention are deformed when their water content is larger than 7%. In addition, after having absorbed more water, they become deliquescent. The stability of the tablets can be ensured by coating them. To evaluate their stability, the tablets of Example 1, Example 4 and Comparative Example 7 were kept at 60° C. and 90% RH for 20 minutes, and the presence or absence of the change in their form was checked. In addition, they were tested for their bitterness by putting them in the mouth for 30 seconds. The test data are shown in Table 2.

TABLE 2

| | Deformation | Bitterness |
|---|---|---|
| Example 1 | no | No |
| Example 4 | no | No |
| Comparative Example 7 | yes | Yes |

The data indicate that the stability of the coated tablets is high and that the coated tablets are easy to take as their bitterness was masked.

The tablets obtained in Examples 5 and 6 were also subjected to the same tests in Test Examples 1 and 2, and produced the same good results.

The non-crosslinked anion exchange resin of formula (I) of the invention exhibits excellent pharmaceutical effects and is useful as a cholesterol depressant for oral administration. According to the tabletting method of the invention, the peroral cholesterol depressant of formula (I) with good pharmaceutical effects can be formed into medicines that are easy to take.

INDUSTRIAL APPLICABILITY

The invention provides anion exchange resin-containing, cholesterol-depressant tablets for oral administration, which are superior to any other conventional ones in that their dose may be decreased and that they are easy to take. In addition, the tabletting method of the invention is greatly advantageous in that it does not require any additional granulating step. The tablets of the invention may be coated with a coating material comprising a cellulosic material, and the resulting coated tablets are easier to take as being not bitter.

The method of the invention is advantageous as being applicable to industrial plants.

What is claimed is:
1. A tablet as formed by mixing an effective amount of non-crosslinked anion exchange resin of formula (I):

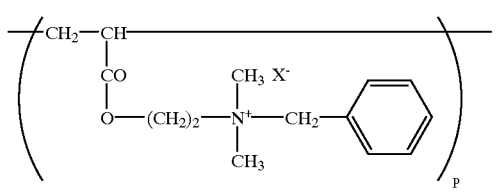

(I)

wherein X represents a physiologically-acceptable counter ion; and p represents an average degree of polymerization, and is larger than 10,000,
from 0.1 to 5% by weight of silicon dioxide and from 1 to 30% by weight of crystalline cellulose, in the absence of water.

2. A tablet of claim 1, wherein silicon dioxide has an apparent specific gravity of from 20 g/liter to 70 g/liter, and crystalline cellulose has a mean grain size of from 10 to 50 microns.

3. A tablet containing an anion exchange resin as formed by coating a non-coated tablet of claim 1 or 2 with a film-forming coating agent.

4. A tablet of claim 3, wherein the coating agent comprises cellulose.

5. A tablet of claim 4, wherein the cellulose is hydroxypropylmethyl cellulose.

6. A tablet of claim 3, wherein the tablet is coated with from 1 to 10% by weight of the coating agent.

7. A tablet of claim 3, wherein the tablet contains less than 7 percent water.

8. A tablet of claim 1, wherein the tablet is coated with from 1 to 10% by weight of a film-forming coating agent and contains less than 7 percent water.

9. A tablet of claim 1, wherein the tablet does not have a bitter taste.

10. A tablet of claim 1, wherein the tablet contains less than 7 percent water and does not have a bitter taste.

11. A tablet of claim 1, wherein the tablet is coated with from 1 to 10% by weight of a film-forming coating agent, contains less than 7 percent water, and does not have a bitter taste.

12. A method for producing a tablet, comprising:
mixing an effective amount of non-crosslinked anion exchange resin of formula (I):

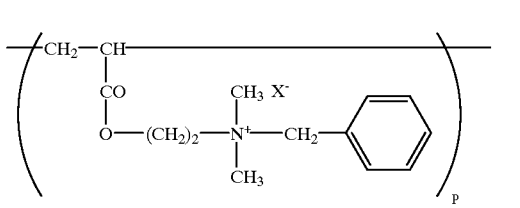

(I)

wherein X represents a physiologically-acceptable counter ion; and p represents an average degree of polymerization, and is larger than 10,000,
from 0.1 to 5% by weight of silicon dioxide and from 1 to 30% by weight of crystalline cellulose, in the absence of water;
and tabletting the resulting mixture.

13. A method of claim 12, wherein silicon dioxide has an apparent specific gravity of from 20 g/liter to 70 g/liter, and crystalline cellulose has a mean grain size of from 10 to 50 microns.

14. A method of claim 12, wherein the formed tablet is coated with a film-forming coating agent.

15. A method of claim 12, wherein the coating agent comprises cellulose.

16. A method of claim 15, wherein the cellulose is hydroxypropylmethyl cellulose.

17. A method of any one of claims 14–16, wherein the tablet is coated with from 1 to 10% by weight of the coating agent.

18. A method of claim 12, wherein the formed tablet contains less than 7 percent water.

19. A method of claim 12, wherein the formed tablet does not have a bitter taste.

* * * * *